United States Patent [19]

Rosenthal

[11] 3,953,526

[45] Apr. 27, 1976

[54] SYNTHESIS OF HYDROQUINONE
[75] Inventor: Rudolph Rosenthal, Broomall, Pa.
[73] Assignee: Atlantic Richfield Company, Los Angeles, Calif.
[22] Filed: Sept. 22, 1972
[21] Appl. No.: 291,418

[52] U.S. Cl. .................. 260/621 H; 260/497 R; 260/617 C
[51] Int. Cl.² ................ C07C 37/00; C07C 37/06
[58] Field of Search ........ 260/488 R, 497 R, 621 H, 260/631 R, 617 C

[56] References Cited
UNITED STATES PATENTS
2,503,641   4/1950   Taytor ........................ 260/621 H
2,640,084   5/1953   Chitwood et al. ............. 260/621 H
3,335,174   8/1967   Norton ......................... 260/631 R X OTHER PUBLICATIONS
Walling et al., "J.A.C.S., " Vol. 85, pp. 2084–2090, (1963).
Noller, "Chem. of Org. Comp.," 3rd Edition, pp. 194–198, (1965).
Titov et al., "CA," Vol. 55, p. 15408d, 1960.

Primary Examiner—Norman Morgenstern
Attorney, Agent, or Firm—John C. Martin, Jr.

[57] ABSTRACT

Cyclohexene is converted to 3,6-diacyloxycyclohexene by reaction with a $C_2$ to $C_6$ aliphatic acyclic saturated carboxylic acid and an organic hydroperoxide in the presence of a copper catalyst. The diacyloxycyclohexene is hydrolyzed to the corresponding dihydroxycyclohexene and dehydrogenated to hydroquinone. For example, with acetic acid the cyclohexene is converted to the 3,6-diacetoxycyclohexene which after hydrolysis and dehydrogenation gives hydroquinone.

13 Claims, No Drawings

SYNTHESIS OF HYDROQUINONE

BACKGROUND OF THE INVENTION

Current methods for producing hydroquinone involve oxidation of aniline with manganese dioxide to quinone followed by reduction with iron dust to hydroquinone or oxidation of diisopropyl benzene to the dihydroperoxide followed by cleavage with acid to hydroquinone.

In the first method large quantities of manganese dioxide are converted to manganese sulfate and, therefore, in order to have a commercially feasible process it is necessary to have a market for the manganese sulfate produced.

In the second method it is necessary to start with highly pure para-diisopropyl benzene and to separate the dihydroperoxide from the monohydroperoxide which is also produced as a by-product. Procedures are available for this separation but they are costly and time-consuming operations. Furthermore, the acid catalyzed conversion of the dihydroperoxide to hydroquinone also produces relatively large amounts of high boiling undesirable by-products.

The instant process not only avoids problems associated with the prior art processes but also has a number of advantages which are distinctly characteristic of the process of the instant invention. The advantages of the instant invention are that readily available starting materials are employed and useful by-products are formed. The organic hydroperoxides are either available commercially or can be prepared readily by air oxidation of the corresponding hydrocarbon. For example, tertiary butyl hydroperoxide is a commercially available product which in the process is reduced to tertiary butyl alcohol and this compound is turn can be used as a gasoline additive or can be dehydrated to isobutylene which is a useful monomer. Cyclohexane can be oxidized to the cyclohexyl hydroperoxide which in the process is reduced to cyclohexanol, this in turn when dehydrated gives cyclohexene which is a starting material used in the invention. Alternatively the cyclohexanol can be used as a precursor for adipic acid production. If ethylbenzene is oxidized to the hydroperoxide it in turn is reduced to the alcohol which when dehydrated produces styrene. If cumene hydroperoxide is employed the alcohol reduction product when dehydrated gives the useful product alphamethylstyrene.

The monocarboxylic acids utilized in the process can be recovered and recycled to the process as will be shown hereinafter. Thus, if acetic acid which is available commercially is employed it can be recovered readily and recycled.

The cyclohexene can either be a recycled product as pointed out or is available by the dehydrogenation of cyclohexane.

Finally, it has been found that essentially no high boiling point by-product compounds are formed by the process of this invention.

SUMMARY OF THE INVENTION

In accordance with the instant invention cyclohexene is reacted with either a secondary or tertiary organic hydroperoxide and a $C_2$ to $C_6$ aliphatic acyclic saturated monocarboxylic acid in the presence of a copper catalyst to produce the corresponding 3,6-diacyloxycyclohexene. The 3,6-diacyloxycyclohexene is hydrolyzed under either acidic or basic conditions to give the corresponding dihydroxycyclohexene. The dihydroxycyclohexene after separation from the hydrolyzing agent is dehydrogenated in the presence of a high boiling solvent and a catalyst such as palladium on carbon to produce the desired hydroquinone.

It is an object of this invention therefore, to provide a method for the synthesis of hydroquinone from cyclohexene.

It is another object of this invention to provide a method for the synthesis of hydroquinone from cyclohexene utilizing relatively inexpensive starting materials and producing useful reaction products in addition to the hydroquinone.

It is another object of this invention to provide a method for the synthesis of hydroquinone from cyclohexene utilizing reactants which can be reprocessed and recycled as starting materials.

Other objects of this invention will be apparent from the following detailed description of the invention and from the claims.

DESCRIPTION OF THE INVENTION

The principal starting material for the process of this invention is cyclohexene, however, this compound need not be in high purity and can be admixed with cyclohexane for example. It is preferable to utilize this compound in as high purity as is commercially feasible, however, in order that the acid and hydroperoxide are not wasted on by-products which also require separation. The cyclohexene is reacted with either a secondary or tertiary hydroperoxide, as has been pointed out, and with a $C_2$ to $C_6$ aliphatic acyclic saturated carboxylic acid in the presence of a copper catalyst. The objective of such reaction is to produce the corresponding 3,6-diacyloxycyclohexene. If the amounts of the hydroperoxide and the carboxylic acid are limited to about 1 mole each per mole of cyclohexene only the monacyloxycyclohexene will be produced. This reaction, however, is shown by Walling et al, JACS, 85, 2084 (1963). Walling et al reacted cyclohexene with acetic acid and either tertiary butyl hydroperoxide or cumene hydroperoxide in the presence of chlorobenzene and cuprous chloride to produce the 3-acetoxycyclohexene.

It has been found that the 3-acyloxycyclohexene produced by the prior art method can be reacted with additional amounts of the acid and hydroperoxide in the presence of the catalyst to produce the 3,6-diacyloxycyclohexene. This latter reaction is not shown in the aforementioned reference. The two-step method for production of the diester is not preferred since this simply adds to the cost of the process, however, since some monoester is produced along with the diester it can be recycled to the process to produce additional diester.

The important discovery of this invention is that the 3,6-diacyloxycyclohexene can be produced in single step utilizing the monocarboxylic acid, organic hydroperoxide and catalysts. That the 3,6-diacyloxy compound can be produced is a novel and surprising discovery since nowhere is such a possibility suggested by Walling et al. Moreover, as has been pointed out, it also has been found that secondary hydroperoxides also can be employed. These discoveries lead to the present complete process as will be shown.

The organic hydroperoxides can be characterized by the formula ROOH wherein the R may be alkyl, cycloalkyl or aralkyl having from 4 to 12 carbon atoms, preferably, and provided that the OOH group is attached to a carbon atom other than an aromatic ring carbon and is either a secondary or a tertiary carbon atom. Tertiary butyl hydroperoxide is a preferred tertiary hydroperoxide and cumene hydroperoxide wherein the hydroperoxide group is attached to the tertiary carbon of the side chain is also an example of a useful tertiary hydroperoxide. Cyclohexyl hydroperoxide is a useful example of a secondary hydroperoxide and also is a cycloalkyl hydroperoxide. Ethylbenzene hydroperoxide is likewise an example of a secondary hydroperoxide wherein the hydroperoxide group is attached to the alkyl group of an aralkyl compound. If isopentane is thermally oxidized with molecular oxygen there is produced a mixture of the tertiary amyl hydroperoxide and the secondary amyl hydroperoxide, either of which or both may be employed in the method of this invention. Substituted compounds also can be employed, for example diisopropyl ketone hydroperoxide. The tertiary hydroperoxides, e.g. tertiary butyl hydroperoxide, tertiary amyl hydroperoxide, and cumene hydroperoxide, because of their stability are particularly suitable, but secondary hydroperoxides, e.g. cyclohexyl hydroperoxide and ethylbenzene hydroperoxides, are also highly suitable since the cyclohexyl hydroperoxide is reduced to the alcohol which when dehydrated gives the cyclohexene, while the ethylbenzene hydroperoxide is reduced to an alcohol which can be readily dehydrated to the highly valuable monomer, styrene. All of these hydroperoxides can be produced conveniently by the thermal oxidation of the corresponding hydrocarbon with molecular oxygen and can be employed in admixture with the unconverted hydrocarbon, the alcohol or other oxidation products generally concurrently produced with the hydroperoxide. Obviously from the standpoint of reducing reactor size it is preferred to use the hydroperoxide in a reasonably concentrated solution.

The acids which can be utilized satisfactorily in the process of this invention are those containing 2 to 6 carbon atoms in the molecule and are aliphatic acyclic monocarboxylic acids. These include acetic acid, propionic acid, butyric acid, pentanoic (valeric) acid and hexanoic (caproic) acid. Acetic acid is the most preferred. It will be understood, of course, that the particular diester obtained depends upon the acid employed. Thus with acetic acid, the 3,6-diacetoxycyclohexene is produced.

The catalysts suitable for use in the production of the 3,6-diacyloxycyclohexene are generally the cuprous salts such as cuprous chloride. However, other cuprous salts such as copper acetate and cupric compounds can be employed. The particular copper compound is not critical and the cuprous chloride is both economical and highly satisfactory.

In general, it is preferred to employ at least 2 moles of the acid and 2 moles of the hydroperoxide per mole of the cyclohexene in order to produce the 3,6-diacyloxycyclohexene. It will be understood, of course, that if amounts in the range of a mole per mole basis are employed as shown in the prior art only the monoester is produced and it is necessary to react the monoacyloxycyclohexene which is the major product with additional acid and hydroperoxide to produce the desired diacyloxycylohexene, thus such amounts are not desired or preferred. Amounts in excess of 2 moles per mole are preferred with amounts ranging up to 3 moles per mole of cyclohexene or more being satisfactory.

The catalysts are employed in the usual catalytic amounts for example, about 0.001 moles of the metal per mole of the cyclohexene, with amounts ranging up to a mole per mole basis if desired. The larger amounts are less preferred since they tend to cause decomposition of the hydroperoxide.

The reaction which produces the diacyloxycyclohexene is carried out at temperature ranging from room temperatures (25° C.) to about 120° C. At the higher temperatures, of course, super-atmospheric pressures are required to maintain a liquid phase reaction system. Temperatures from 50° C. to 100° C. are preferred since at these temperatures the hydroperoxides are in a more stable range and do not undergo ordinary thermal decomposition. While pressures can range from sub-atmospheric to super-atmospheric, it is preferred to use atmospheric or slightly super-atmospheric pressure to maintain a completely liquid phase reaction system.

The diester can be hydrolyzed either under acidic or basic conditions, for example the hydrolysis may be carried out using aqueous sodium hydroxide or aqueous sulfuric acid. However, it has been found that when using these methods it is difficult to isolate the dihydroxycyclohexene product because of the high solubility of such product in the aqueous solution. Alternatively, therefore, it is preferred to use ion exchange resins, either a cation exchange resin in the hydrogen (acid) form, or an anion exchange resin in the hydroxyl (basic) form. These can be employed in aqueous or aqueous-alcoholic solution. The resin is filtered off and the dihydroxycyclohexene is recovered by solvent extraction or by distillation. Another method which can be used is treatment with a solution of potassium hydroxide, for example, in ethanol. In this method the recovery of the desired dihydroxycyclohexene is accomplished by first removing the ethanol by vacuum distillation and thereafter distilling the product at a pressure below about 1 mm Hg. The hydrolysis is conventionally carried out at ordinary room temperature (25° C.) by simply stirring the diester with the ethanolic alkali metal hydroxide solution. Higher temperatures can be employed but are not necessary.

The 3,6-dihydroxycyclohexene product is dehydrogenated preferably in the liquid phase by dissolving it in a high boiling solvent and heating in contact with a mild dehydrogenation catalyst such as palladium on carbon. The solvents which can be employed include those which are inert to dehydrogenation, such as high boiling glycol ethers for example, bis[2-(2-methoxyethoxy)ethyl] ether. The high boiling hydrocarbons such as the polynuclear and condensed polynuclear aromatics for example, biphenyl, the orthometa-, and para-terphenyls, anthracene, phenanthrene and the like and also other high boiling ethers, such as diphenyl ether. These high boiling solvents, i.e. boiling above about 225° C., are preferred since it is desired to carry out the dehydrogenation at temperatures in a range of from 150° C. to 300° C. preferably 200° C. to 250° C. in the liquid phase.

The catalysts which can be employed in addition to the palladium on carbon wherein the palladium generally amounts to about 5 weight per cent also include other commercial catalysts such as nickel on kieselguhr, palladium on magnesia and sulfur. The particular dehydrogenation catalyst is not a critical feature since the dehydrogenation proceeds under very mild conditions. In fact the dehydrogenation proceeds so readily that great care must be taken to avoid acidic sites on the catalyst which would cause complete dehydration and even ring cracking. Thus it is desirable to treat the catalyst with a mild basic solution, either inorganic or organic to insure there are no acidic sites on the catalyst which would cause dehydration or even cracking. The presence of the unsaturation in the ring of the dihydroxycyclohexene makes it readily susceptible to dehydrogenation to hydroquinone, but likewise susceptible to complete dehydration or even cracking, hence the mild conditions and catalysts described must be employed.

The amount of catalyst is in the range of ordinary catalytic amounts, for example if 5 percent palladium on carbon is employed the amount of catalyst can be conveniently 10 weight percent of the weight of the dihydroxycyclohexene being dehydrogenated. In general the amount of catalyst can range from 0.5 weight percent or less to 25 weight percent or more and the reaction can be carried out either in batch or continuous systems.

The hydroquinone can be recovered from water immiscible solvents by conventional method from the dehydrogenation reaction mixture, such as water extraction followed by stripping the water from the hydroquinone and crystallization methods, all of which are well known in the art. When the water soluble glycol ethers are employed conventional fractional distillation methods can be used to recover the hydroquinone.

The following Examples are provided for the purpose of illustrating the invention in additional detail.

EXAMPLE I (Prior Art)

In order to provide a quantity of the 3-acetoxycyclohexene compound the prior art method was employed. A mixture of 200 g. (2.44 moles) cyclohexene, 100 g. (1.67 moles) acetic acid and 0.5 g. cuprous chloride was heated in an oil bath to 80° C. During a 1 hour period 60 g. of 90.5 weight percent purity tertiary butyl hydroperoxide (0.6 moles) was added dropwise keeping the temperature at 80° C. After 3 hours the mixture analyzed 3.8 weight percent tertiary butyl hydroperoxide and after 6 hours 0.05 weight percent tertiary butyl hydroperoxide. Analysis by gas-liquid phase chromatography (glpc) indicated that an 81 mole percent selectivity to 3-acetoxycyclohexene was obtained at a 97 percent conversion of the hydroperoxide. The product was recovered by dissolving the mixture in n-hexane, water extraction to remove acetic acid, t-butanol and unreacted hydroperoxide and, finally distillation at 50° C. at 5 mm Hg pressure. The yield of recovered product was in excellent agreement with the analytical value and only a very little high boiling residue was formed.

EXAMPLE II

Using the method of Example I, a mixture of 28 g. cyclohexene, 10 g. acetic acid, 10 g. of 48 weight percent purity cyclohexyl hydroperoxide and 0.07 g. cuprous chloride was heated at 80° C. for 5 hours. The hydroperoxide was all converted at this time and glpc analysis showed a 68 mole percent yield of 3-acetoxycyclohexene. This example merely shows that secondary hydroperoxides (not shown in the prior art) can be used to make the monoester.

EXAMPLE III

A mixture of 14 g. of the 3-acetoxycyclohexene produced in Example I, 14 g. acetic acid and 0.2 g. cuprous chloride was heated to 80° C. Tertiary butyl hydroperoxide, 10 g. of 93 weight percent purity tertiary butyl hydroperoxide was added dropwise to maintain the temperature at 80° C. After 6 hours, analysis showed that the selectivity to the 3,6-diacetoxycyclohexene was 36.5 weight percent based on 3-acetoxycyclohexene converted. It was also found that cyclohexyl hydroperoxide could be substituted for the tertiary butyl hydroperoxide in this reaction. These runs demonstrate the feasibility of recycle of the monoester, if produced with the diester.

EXAMPLE IV

In order to demonstrate that the 3,6-diacyloxycyclohexene can be prepared in a single step procedure, a mixture of 20.5 g. (0.25 moles) cyclohexene, 45 g. (0.75 moles) acetic acid and 45 g. of 90.5 weight percent purity tertiary butyl hydroperoxide (0.45 moles) and 0.4 g. cuprous chloride was heated at 80° – 85° C. for 10 hours at which time it was found that 97 weight percent of the hydroperoxide had been consumed. Analysis by glpc showed that 21 mole percent yield to 3-acetoxycyclohexene and a 25 mole percent yield to 3,6-diacetoxycyclohexene was obtained. The reaction mixture was treated as in Example I and the product distilled at 92° C. under 1 mm Hg pressure. Very little high boiling residue was found. It will be noted that although 0.5 moles of the hydroperoxide solution was used since it was not pure only 0.45 moles of the hydroperoxide itself was employed, i.e. slightly less than the desired 2:1 mole ratio of hydroperoxide to cyclohexene, a good yield of the diester was obtained.

In a similar run it was found that cyclohexyl hydroperoxide could be substituted for the tertiary butyl hydroperoxide in this reaction. In this run 5 g. cyclohexene, 15 g. acetic acid and 0.05 g. cuprous chloride was heated to 80° C. and, thereafter, 22 g. of 48 weight percent purity cyclohexyl hydroperoxide was added dropwise over a 45 min. period maintaining the temperature at 80° C. At the end of 6 hours glpc analysis showed the formation of 2.9 g. of 3-acetoxycyclohexene and 0.42 g. of 3,6-diacetoxycyclohexene.

EXAMPLE V

In order to produce the 3,6-dihydroxycyclohexene a mixture of 2.4 g. potassium hydroxide, 20 g. ethanol, and 4 g. of the 3,6-diacetoxycyclohexene was stirred at room temperature for 3 hours. The ethanol was removed under vacuum and the product distilled at a pressure below 1 mm Hg. The distillate was identified by nuclear magnetic resonance (NMR) spectroscopy and mass spectroscopy (MS) as the 3,6-dihydroxycyclohexene. In similar experiments it was also shown that the hydrolysis could be carried out using aqueous sodium hydroxide or aqueous sulfuric acid; however, in these cases it was difficult to isolate the dihydroxycyclohexene product because of its high solubility in aqueous solution.

Similar hydrolysis runs were carried out utilizing anion exchange resins in the hydroxyl form and cation exchange resins in the hydrogen form and in all runs hydrolysis of the diester to the dihydroxycyclohexene was obtained. These runs demonstrate that the diester can be hydrolyzed readily to the dihydroxy compounds.

When acid hydrolysis is employed the acid corresponding to the original acid is produced and can be recovered by ordinary known methods such as distillation.

If basic hydrolysis is used the salt of the acid is produced. After recovery of the 3,6-dihydroxycyclohexene the solution can be acidified and the acid recovered by distillation.

EXAMPLE VI

In order to show conversion of the 3,6-dihydroxycyclohexene to hydroquinone a run was carried out wherein 1 g. of 3,6-dihydroxycyclohexene obtained in Example V was dissolved in 2 ml of bis[2-(2-methoxyethoxy)ethyl] ether and 0.1 g. of a commercial 5 percent by weight palladium on carbon catalyst was added. The mixture was heated at 220° C. for 4 hours and the product obtained was identified as hydroquinone by both NMR and MS analysis.

The foregoing Examples demonstrate the operability and utility of the invention. These Examples also show that a reaction time of from about 1 hour to about 12 hours is preferred for the diester formation in the temperature range specified. In the hydrolysis at room temperatures times ranging from ½ hour to 5 hours are required. In the dehydrogenation reaction times ranging from about 1 hour to 10 hours are suitable, the times being dependent upon the severity of the reaction conditions and the activity of the catalyst employed. It should be pointed out, however, that no extensive engineering runs were made to optimize all of the conditions to maximize yields as would be done to commercialize the process, however, the ranges of reaction conditions, the types and amounts of reactants and catalysts are fully set forth such as to enable one skilled in the art to optimize the yield of hydroquinone from cyclohexene and to recover any of the various possible valuable and useful by-products of the reaction while substantially completely eliminating any non-useful or wasteful by-products.

I claim:

1. A method for the production of hydroquinone from cyclohexene which comprises
   a. contacting cyclohexene with $C_2$ to $C_6$ aliphatic monocarboxylic acid selected from the group consisting of acetic acid, propionic acid, butyric acid, pentanoic acid, and hexanoic acid and a secondary or tertiary organic hydroperoxide having the formula ROOH wherein R may be alkyl, cycloalkyl or aralkyl in the presence of a copper compound as the catalyst in the liquid phase at a temperature in the range of from about 25° C. to 120° C. to produce a 3,6-diacyloxycyclohexene wherein at least 2 moles of said acid and 2 moles of said hydroperoxide are employed per mole of cyclohexene,
   b. hydrolyzing the 3,6-diacyloxycyclohexene to 3,6-dihydroxycyclohexene and
   c. catalytically dehydrogenating the 3,6 dihydroxycyclohexene to hydroquinone.

2. The method according to claim 1, wherein the monocarboxylic acid is acetic acid and the catalyst is a cuprous salt.

3. The method according to claim 2, wherein the organic hydroperoxide is tertiary butyl hydroperoxide and the catalyst is cuprous chloride.

4. The method according to claim 2, wherein the organic hydroperoxide is cyclohexyl hydroperoxide and the catalyst is cuprous chloride.

5. The method according to claim 1, wherein the temperature for the production of 3,6-diacyloxycyclohexene is in the range of from 50° C. to 100° C.

6. The method according to claim 1, wherein the hydrolyzing step is carried out by the use of an anion exchange resin in the hydroxyl form.

7. The method according to claim 1, wherein the hydrolyzing step is carried out by the use of a cation exchange resin in the hydrogen form.

8. The method according to claim 1, wherein the hydrolysis is carried out by the use of ethanol solution of potassium hydroxide.

9. The method according to claim 1, wherein the catalytic dehydrogenation of the 3,6-dihydroxycyclohexene to hydroquinone is carried out in the presence of a palladium on carbon catalyst and a solvent boiling above about 225° C.

10. The method according to claim 9, wherein the solvent is bis[2-(2-methoxyethoxy)ethyl]ether.

11. The method according to claim 9, wherein the high boiling solvent is a polynuclear aromatic hydrocarbon.

12. The method according to claim 1, wherein the monocarboxylic acid is acetic acid, the organic hydroperoxide is tertiary butyl hydroperoxide, the catalyst is cuprous chloride, the hydrolysis is carried out with an ethanol solution of potassium hydroxide and catalytic dehydrogenation is carried out with palladium on carbon catalyst in the presence of a solvent boiling above 225° C.

13. The method according to claim 1, wherein the monocarboxylic acid is acetic acid, the organic hydroperoxide is cyclohexyl hydroperoxide, the catalyst is cuprous chloride, the hydrolysis is carried out with an ethanol solution of potassium hydroxide and catalytic dehydrogenation is carried out with palladium on carbon catalyst in the presence of a solvent boiling above 225° C.

* * * * *